United States Patent [19]
Forster

[11] 4,456,826
[45] Jun. 26, 1984

[54] ROTATING DETECTOR SYSTEM WITH COOLANT SUPPLY

[75] Inventor: Helmut Forster, Neunkirchen, Fed. Rep. of Germany

[73] Assignee: Siemens Aktiengesellschaft, Munich, Fed. Rep. of Germany

[21] Appl. No.: 429,868

[22] Filed: Sep. 30, 1982

[30] Foreign Application Priority Data

Dec. 15, 1981 [DE] Fed. Rep. of Germany ....... 3149705

[51] Int. Cl.$^3$ .......................... G01T 1/24; G03B 41/16
[52] U.S. Cl. .................................. 250/370; 62/514 R; 378/19
[58] Field of Search ................. 378/19; 250/370, 371; 62/381, 514 R

[56] References Cited

U.S. PATENT DOCUMENTS 3,609,992  10/1971  Cacheux ........................... 250/370

Primary Examiner—Alfred E. Smith
Assistant Examiner—Carolyn E. Fields
Attorney, Agent, or Firm—Kenyon & Kenyon

[57] ABSTRACT

In an arrangement for preparing a sectional image of the body, the picture elements of which are derived from the absorption of ionizing rays, the detector system contains detectors associated with a cooling system having a cooling finger against which the cooling surfaces of the detectors rest and which is connected via a cryogenic line to two coolant tanks which are arranged in the plane of motion of the detector system centrally symmetric to the center of rotation. As a result the rotating detector system with the coolant supply requires no automatic mass equalization device adapted to the consumption of coolant, and the cooling system can be designed for different operating times.

7 Claims, 2 Drawing Figures

ROTATING DETECTOR SYSTEM WITH COOLANT SUPPLY

BACKGROUND OF THE INVENTION

This invention relates to an arrangement for preparing a sectional image of the body, the picture elements of which are derived from the absorption of ionizing rays which penetrate a respective body element in the sectional body plane in different directions, with a rotating detector system which contains detectors arranged side by side in the plane of motion.

Image generating systems, such as computer tomography systems, with detectors have the primary purpose in medical diagnostics of representing the anatomy of the patient as faithfully as possible. The three-dimensional resolution should be as high as possible, as should the contrast with which adjacent organs or vessels are delineated from each other. The exposure time must be short enough to eliminate motion influences.

If germanium detectors which have particularly high resolution are used, cooling with liquid gas is necessary to reduce the detector noise to negligible values. For cooling, the detectors are generally arranged on a cold surface, the back side of which is thermally connected to a cold reservoir. Continuous cooling, however, presents technical difficulties, since the detector bodies must not only be cooled during operation, but must also be arranged in a vacuum.

It is now an object of the present invention to provide a rotating detector system with a coolant supply which requires no automatic mass equalization devices adapted to the consumption of coolant.

SUMMARY OF THE INVENTION

This object is achieved in an arrangement for preparing a sectional image of the body of the type mentioned above with detector systems containing individual detectors, associated with a cooling system having a cooling finger against which the cooling surfaces of the detectors rest and which is connected via a cryogenic line to two coolant tanks which are arranged in the plane of motion of the detector system centrally symmetric to the center of rotation. This arrangement with the two supply tanks is moved at high speed about the object to be examined, for instance, a patient. The detectors arranged in a row on the cooling finger can preferably be pressed against the cooling finger by insulators and clamps. Thereby, a good thermal transition is obtained.

The coolant, for instance, liquid nitrogen is taken uniformly from the two tanks by the centrifugal force and by an adjustable regulating and control pressure and arrives in the liquid state at an inlet nozzle of the detector system which contains the cooling finger. The cooling finger is designed so that the coolant can transfer its heat of evaporation to the detectors, i.e. the coolant leaves the cooling finger via the outlet nozzle in the gaseous state.

DETAILED DESCRIPTION

Figure 1:
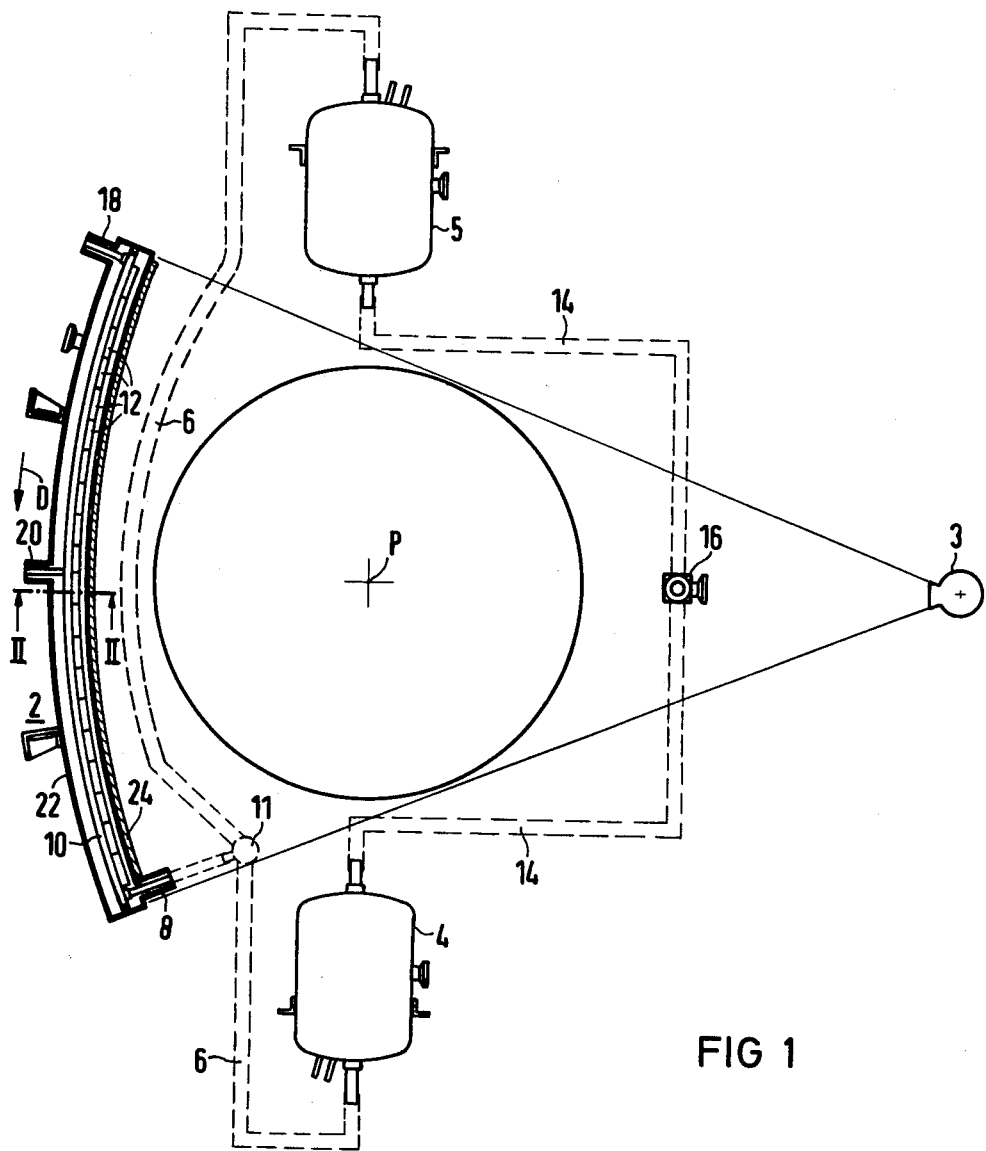
FIG. 1 is an overall view of an embodiment of an arrangement for preparing a sectional image of the body with a detector system according to the present invention shown schematically.

In the embodiment according to FIG. 1, a rotating detector system 2, two coolant supply tanks 4 and 5, the center of rotation of the system P and the radiation source 3, which furnishes a fan-shaped ray bundle with the aid of an aperture, are illustrated. Via a cryogenic line 6 the coolant gets from the two coolant supply tanks 4 and 5, to the input nozzle 8 of the cooling finger 10. On the cooling finger 10, detectors 12 having a semiconductor body of highest purity monocrystalline germanium are arranged side by side. The two coolant supply tanks 4 and 5 are connected to each other via a cryogenic line 14 and a pressure regulator 16. The cooling finger 10 is connected cryogenically to the outer jacket 22 at the inlet nozzle 8, an outlet nozzle 18 and a support 20. On the side of the outer jacket 22 facing the fulcrum P, a window 24 is provided which may consist, for instance, of a composite alloy steel/aluminum material. In this embodiment, the coolant, e.g. the liquid nitrogen, is transported by centrifugal force from the two supply tanks 4 and 5 into the cryogenic line 6 and is then pushed against the centrifugal force to the junction point 11. From there, the coolant flows, due to the centrifugal force, which is dependent on the speed of rotation, to the inlet nozzle 8 of the cooling finger 10. The coolant is pumped against the direction of rotation which is indicated by an arrow D in the Figure, through the cooling finger 10 by a force and in the process gives off its heat of evaporation. This force is composed of several individual forces, namely, the centrifugal force which depends on the speed of rotation and the radius, the pressure in the line which is generated by the regulating and control pressure in the supply tank, and the pressure difference in the cooling finger, which depends on the distances of the beginning and the end of cooling finger from the center of rotation P.

The section between the cooling finger inlet and the outlet, along which the coolant changes its state from the liquid to the gaseous state, forms a thermal resistance.

With this arrangement the rotating detector system with a coolant supply requires no automatic mass equalization device adapted to the consumption of coolant, and the cooling system can be designed for different operating times.

Figure 2:
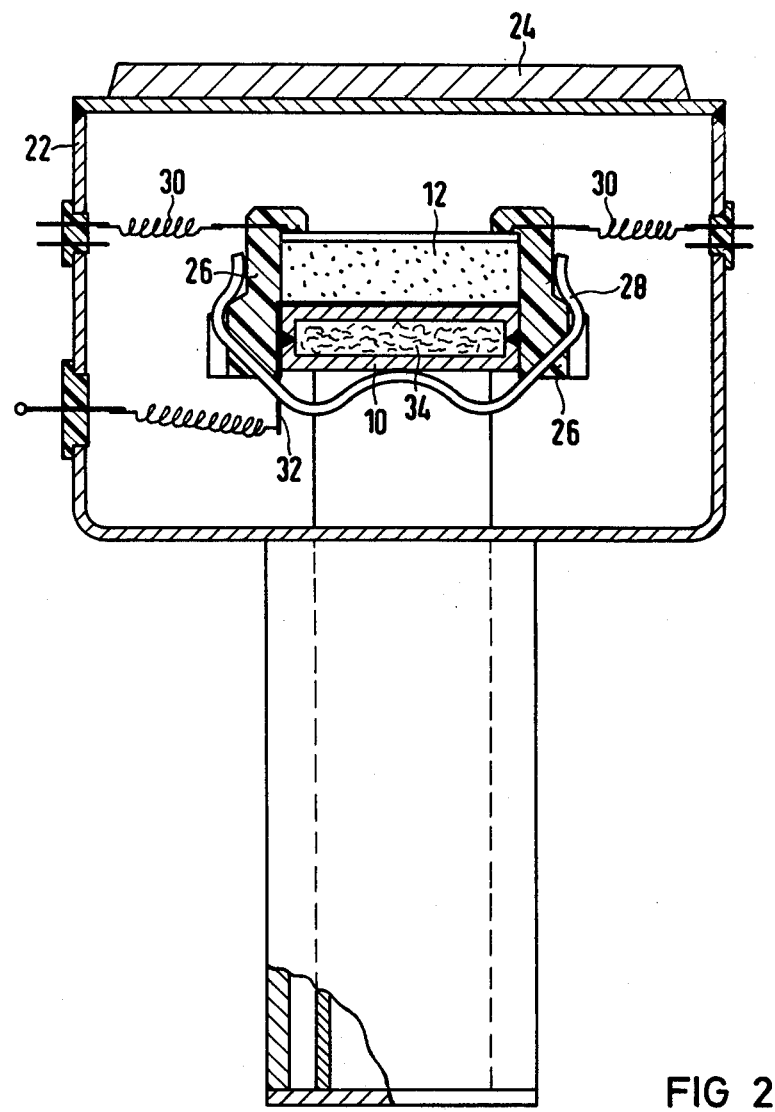
FIG. 2 is a cross section of the detector system.

In the embodiment of the cooling system 2 according to FIG. 2, the detectors 12 are pressed onto the cooling finger 10 by insulators 26 and 28. Contact springs 30 are provided for making electrical contact with the detectors 12. In addition, a foil 32 is arranged between the detectors 12 and the cooling finger 10. Foil 32 consists of a highly heat conducting and electrically conductive material and may be connected to an electrical connecting lead, not specifically designated in the Figure, which is brought out of the outer jacket 22 with a vacuumtight feedthrough. The cooling finger 10 is a rectangular hollow member which preferably has its interior filled with chips 34 which may consist, for instance, of copper or also alloy steel wool. The chips 34 in the interior of the cooling finger 10 improve the heat exchange between the coolant and the detectors 12.

This arrangement is surrounded in a vacuumtight manner by the outer jacket 22 which preferably consists of alloy steel and may be provided with an alloy steel/aluminum window 24. With this design, a good thermal transition between the detectors 12 and the cooling finger 10 is obtained.

What is claimed is:

1. In an arrangement for preparing a sectional image of the body, the picture elements of which are derived from the absorption of iodizing rays which penetrate the corresponding body element in a sectional body plane in different directions, with a rotating detector system which contains detectors arranged side by side in the plane of motion, the improvement comprising:
  (a) the detector system containing individual detectors;
  (b) a cooling system provided with a cooling finger against which cooling surfaces of said detectors rest;
  (c) two coolant tanks which are arranged in the plane of motion of the detector system centrally symmetric to its center of rotation; and
  (d) a cryogenic line connecting said tanks to said cooling system.

2. The improvement according to claim 1, wherein said cooling finger and said detectors are arranged in a vacuum.

3. The improvement according to claim 1, wherein said detector system comprises detectors with a semiconductor body of highest purity monocrystalline germanium, and wherein liquid nitrogen is the coolant.

4. The improvement according to claim 1, wherein said cooling finger is designed as a thermal resistance.

5. The improvement according to claim 1, wherein the detectors are fastened on the cooling finger by means of insulators and clamps.

6. The improvement according to claim 1, wherein said cooling finger has inlet and outlet nozzles, said nozzles cryogenically connected to an outer jacket of the detector system.

7. The improvement according to claim 6, and further including a window made of composite alloy steel/aluminum in the outer jacket pointing toward the center of rotation.

* * * * *